US006737548B2

(12) United States Patent
Inoki et al.

(10) Patent No.: US 6,737,548 B2
(45) Date of Patent: May 18, 2004

(54) PROCESS FOR PREPARING 1,5-DIAMINONAPHTHALENE DERIVATIVE

(75) Inventors: Satoshi Inoki, Yamaguchi (JP); Yoshio Motoyama, Hiroshima (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/312,852

(22) PCT Filed: May 2, 2002

(86) PCT No.: PCT/JP02/04398

§ 371 (c)(1),
(2), (4) Date: Jan. 2, 2003

(87) PCT Pub. No.: WO02/090315

PCT Pub. Date: Nov. 14, 2002

(65) Prior Publication Data

US 2003/0176722 A1 Sep. 18, 2003

(30) Foreign Application Priority Data

| May 8, 2001 | (JP) | 2001-136962 |
| May 30, 2001 | (JP) | 2001-161619 |
| Sep. 7, 2001 | (JP) | 2001-271763 |

(51) Int. Cl.[7] ................... C07C 209/36; C07C 209/40; C07C 211/57; C07C 211/59
(52) U.S. Cl. ..................................... 564/308
(58) Field of Search ........................... 564/308

(56) References Cited

U.S. PATENT DOCUMENTS

| 3,787,496 A | 1/1974 | Whitney et al. |
| 5,113,025 A | 5/1992 | Park et al. |

| 2002/0103401 A1 | 8/2002 | Schelhaas et al. |

FOREIGN PATENT DOCUMENTS

| EP | 0 050 229 A1 | 4/1982 |
| EP | 0 495 432 A1 | 7/1992 |
| JP | 51-70757 | 6/1976 |
| JP | 59-29061 B2 | 7/1984 |
| JP | 6-87746 A | 3/1994 |
| JP | 7-278066 A | 10/1995 |
| WO | WO 99/12887 A1 | 3/1999 |
| WO | 02/51792 A1 | 7/2002 |

OTHER PUBLICATIONS

Janin, Yves L. et al., "A New Access to 1–Naphthylamines by an Equivalent Semmler–Wolff Reaction," Synthesis, 1 pp. 57–59 1993.
German Application No. 100 64 779.0 filed Dec. 22, 2000.

*Primary Examiner*—Brian Davis
(74) *Attorney, Agent, or Firm*—Burns, Doane, Swecker & Mathis, LLP

(57) ABSTRACT

In a process where an ortho-alkylnitrobenzene derivative and a vinyl compound as starting materials are used to prepare a 1,5-diaminonaphthalene derivative via a 4-(2-nitrobenzene)propane derivative and a 5-nitro-1-tetralone derivative, the ortho-alkylnitrobenzene derivative and a vinyl compound having an electron withdrawing group such as an acrylonitrile derivative and an acrylate may be reacted in the presence of a base to provide an aromatic nitro compound. An aromatic nitro compound such as 4-(2-nitrobenzene)butanonitrile thus obtained may be cyclized to safely, cost-effectively and selectively provide a 5-nitro-1-tetralone derivative without forming any isomer. Furthermore, from the 5-nitro-1-tetralone derivative, a 1,5-diaminonaphthalene derivative may be prepared without forming any isomer.

21 Claims, No Drawings

PROCESS FOR PREPARING 1,5-DIAMINONAPHTHALENE DERIVATIVE

This application is a 371 of PCT/JP02/04398 filed May 2, 2002.

TECHNICAL FIELD

The present invention relates to a process for preparing a 1,5-diaminonaphthalene derivative. In particular, it relates to a process for preparing a 1,5-diaminonaphthalene derivative using a 5-nitro-1-tetralone derivative as starting material. A 1,5-diaminonaphthalene derivative prepared according to the process of this invention is useful as a material for a variety of synthetic resins. For example, a 1,5-diaminonaphthalene derivative may be reacted with phosgene to form a diisocyanate, which may be then converted into a polyurethane resin, a dicarboxylic acid or its derivative to provide a polyamide resin.

BACKGROUND OF THE INVENTION

Conventionally, a 1,5-diaminonaphthalene derivative has been prepared by nitrating naphthalene to produce a dinitronaphthalene and then reducing the nitro groups into amino groups. Dinitration of naphthalene, however, produces a 1,8-dinitro derivative in a large amount in addition to the desired 1,5-dinitro derivative. For example, in nitration of 1-nitronaphthalene in a chlorine-containing organic solvent as described in Japanese Laid-open Patent Publication No. 51-070757, 1,5-dinitronaphthalene is produced in an yield of 30% while 1,8-dinitronaphthalene in an yield of 65%. That is, the 1,8-dinitro derivative is formed in a two-fold or more amount of the 1,5-dinitro derivative. 1,8-Dinitronaphthalene may be readily reduced into 1,8-diaminonaphthalene, which may be, for example, used as a material for a dye. However, when a demand for 1,8-diaminonaphthalene is reduced, production of 1,5-dinitronaphthalene is reduced, making 1,5-diaminonaphthalene less available.

In the light of such status, there have been attempts for increasing an yield of the 1,5-derivative in nitration of naphthalene. For example, WO 99-12887 has described that using Nafion® as an acid, 1-nitronaphthalene is nitrated with nitric acid to give 1,5- and 1,8-dinitronaphthalenes in yields of 34.1% and 38.0%, respectively. Thus, the proportion of the 1,5-dinitro derivative may be improved, but the 1,8-derivative is still formed in a large amount.

As described above, the current preparation procedure produces the 1,8-dinitro derivative in a large amount in addition to the 1,5-dinitro derivative. Thus, there has been needed to provide a process for selectively producing a 1,5-diaminonaphthalene derivative without forming isomers.

Besides the process involving dinitration of naphthalene and reduction of the nitro groups, many alternative processes have been suggested; for example, amination of 1,5-dihydroxynaphthalene as a starting material (U.S. Pat. No. 5,113,025, Japanese Laid-open Patent Publication No. 59-29061), amination of a 5-halogeno-1-aminonaphthalene or 1,5-dihalogenonaphthalene (Japanese Laid-open Patent Publication No. 7-278066, U.S. Pat. No. 3,787,496) and amination of sodium 1,5-naphthalenedisulfonate (Nihon Kagakukai Shi, 522 (1974)). However, a cumene process for preparing 1,5-dihydroxynaphthalene tends to cause rearrangement of a isopropyl group in 1,5-diisopropylnaphthalene as a starting material to the β-position due to steric hindrance, leading to formation of isomers as is in the process involving dinitration and reduction. It is, therefore, not a selective method. Halogenation or sulfonation of naphthalene is also less selective.

SUMMARY OF THE INVENTION

We have intensely investigated for providing a process for selectively preparing a 1,5-diaminonaphthalene derivative without forming isomers, and have found a process for preparing a 1,5-diaminonaphthalene derivative using a 5-nitro-1-tetralone derivative as an intermediate, achieving this invention.

Specifically, this invention comprises the embodiments described in the following [1] to [7].

[1] A process for preparing a 1,5-diaminonaphthalene derivative comprising:

(i) the first step comprising reacting an ortho-alkylnitrobenzene represented by formula (1):

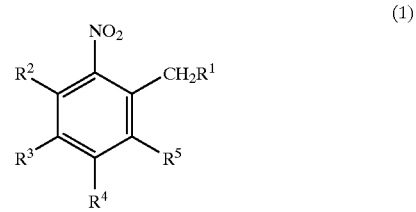

wherein $R^1$ to $R^4$, which may be the same or different, represent hydrogen, alkyl having 1 to 4 carbon atoms, aromatic hydrocarbon having 6 to 12 carbon atoms, or halogen; and $R^5$ represents hydrogen, with a vinyl compound represented by formula (2):

wherein $R^6$ and $R^7$, which may be the same or different, represent hydrogen, alkyl having 1 to 4 carbon atoms, or halogen; and X represents an electron withdrawing group, provided that $R^6$ and $R^7$ are mutually cis- or trans-configured, in the presence of a base, to produce an aromatic nitro compound represented by formula (3):

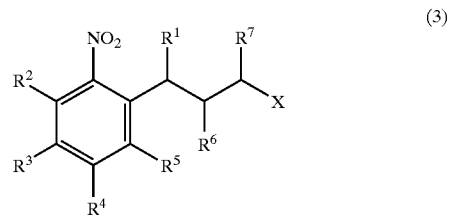

wherein $R^1$ to $R^7$ are as defined in formulas (1) and (2); and X represents an electron withdrawing group, which may be the same as or different from X as defined in formula (2);

(ii) the second step of cyclizing the aromatic nitro compound represented by formula (3) to produce a 5-nitro-1-tetralone derivative represented by formula (4):

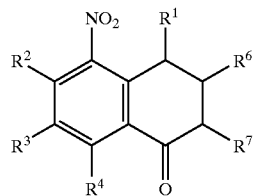

(4)

wherein $R^1$ to $R^4$ and $R^6$ to $R^7$ are as defined in formulas (1) and (2); and (iii) the third step comprising reacting the 5-nitro-1-tetralone derivative represented by formula (4) with an amine to provide an intermediate, which is then reduced and aromatized to produce the 1,5-diaminonaphthalene derivative represented by formula (5):

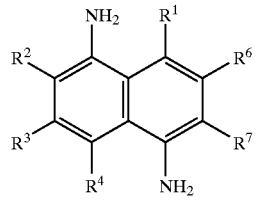

(5)

wherein $R^1$ to $R^4$ and $R^6$ to $R^7$ are as defined in formulas (1) and (2).

[2] The process as described in [1], wherein X in formula (2) is one selected from the group consisting of CN and $CO_2R^8$ where $R^8$ represents alkyl having 1 to 7 carbon atoms, cycloalkyl, aromatic hydrocarbon having 6 to 12 carbon atoms or aralkyl.

[3] The process as described in [1], wherein X in formula (3) is one selected from the group consisting of $CONH_2$, CN, $CO_2H$ and $CO_2R^8$ where $R^8$ represents alkyl having 1 to 7 carbon atoms, cycloalkyl, aromatic hydrocarbon having 6 to 12 carbon atoms or aralkyl.

[4] The process as described in [1] or [2], wherein the reaction of the ortho-alkylnitrobenzene represented by formula (1) with the vinyl compound represented by formula (2) in the first step is conducted in the presence of at least one selected from the group consisting of a solvent capable of dissolving at least part of the base and a catalyst capable of solubilizing the base.

[5] The process as described in [4], wherein the solvent capable of dissolving at least part of the base is a circular urea derivative.

[6] The process as described in any of [1] to [5], wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

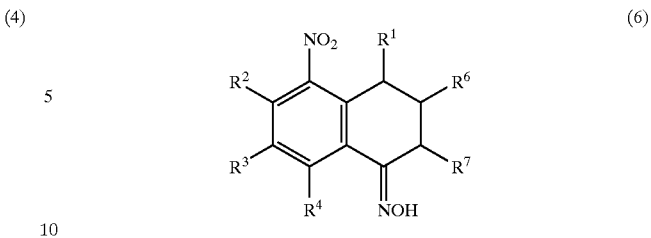

wherein $R^1$ to $R^4$ and $R^6$ to $R^7$ are as defined in formulas (1) and (2), which is then converted by aromatization into a 5-nitro-1-aminonaphthalene derivative represented by formula (7):

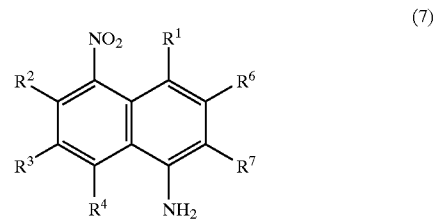

wherein $R^1$ to $R^4$ and $R^6$ to $R^7$ arc as defined in formulas (1) and (2), which is then reduced into the 1,5-diaminonaphthalene derivative represented by formula (5).

[7] The process as described in any of [1] to [5], wherein in the third step, an ammonia derivative as the amine is reacted with the 5-nitro-1-tetralone derivative represented by formula (4) to provide an imine represented by formula (8):

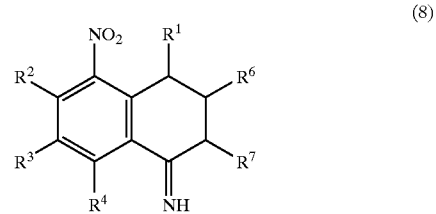

wherein $R^1$ to $R^4$ and $R^6$ to $R^7$ are as defined in formulas (1) and (2), which is then reduced and aromatized to provide the 1,5-diaminonaphthalene derivative represented by formula (5).

The above process wherein an ortho-alkylnitrobenzene derivative and a vinyl compound are used as starting materials to give a 5-nitro-1-tetralone derivative, from which a corresponding 1,5-diaminonaphthalene derivative is prepared, allows the 1,5-diaminonaphthalene derivative to be selectively prepared without forming isomers.

DETAILED DESCRIPTION OF THE INVENTION

First, there will be described the first step in the process according to this invention, in which an ortho-alkylnitrobenzene derivative is reacted with a vinyl compound to prepare an aromatic nitro compound.

In the present invention, in formula (1), $R^1$ to $R^4$ may be the same or different, and represent hydrogen, alkyl having 1 to 4 carbon atoms, aromatic hydrocarbon having 6 to 12 carbon atoms or halogen; and $R^5$ represents hydrogen.

In the present invention, in formula (2), $R^6$ and $R^7$ may be the same or different, and represent hydrogen, alkyl having 1 to 4 carbon atoms or halogen; X represents an electron withdrawing group; and $R^6$ and $R^7$ are mutually cis- or trans-configured.

Examples of alkyl in $R^1$ to $R^4$ and $R^6$ and $R^7$ include methyl, ethyl, n-propyl, isopropyl, n-butyl, i-butyl and t-butyl.

Examples of aromatic hydrocarbon in $R^1$ to $R^4$ include phenyl, tolyl and xylyl.

Examples of halogen in $R^1$ to $R^4$ and $R^6$ and $R^7$ include fluorine, chlorine, bromine and iodine.

In formula (2), $R^8$ when X is $CO_2R^8$ represents alkyl having 1 to 7 carbon atoms, cycloalkyl, aromatic hydrocarbon having 6 to 12 carbon atoms, or aralkyl. Examples of alkyl having 1 to 7 carbon atoms include methyl, ethyl, n-propyl, isopropyl, n-butyl, i-butyl, t-butyl, n-pentyl and n-hexyl. Examples of cycloalkyl include cyclopentyl and cyclohexyl. Example of aromatic hydrocarbon include phenyl, tolyl and xylyl. Examples of aralkyl is benzyl and phenethyl.

In the present invention, examples of an ortho-alkylnitrobenzene derivative represented by formula (1) include 2-methylnitrobenzene, 2-methyl-6-isopropylnitrobenzene, 2-methyl-5-t-butylnitrobenzene, 2,4-dimethylnitrobenzene, 2-methyl-4-chloronitrobenzene, 2-ethylnitrobenzene and 2-benzylnitrobenzene.

In the present invention, examples of an electron withdrawing group X in a vinyl compound represented by formula (2) is preferably one selected from the group consisting of CN and $CO_2R^8$ where $R^8$ represents alkyl having 1 to 7 carbon atoms, cycloalkyl, aromatic hydrocarbon having 6 to 12 carbon atoms or aralkyl. Examples of an acrylonitrile derivative in which X is CN include acrylonitrile, methacrylonitrile, crotononitrile, 2-chloroacrylonitrile, 3-chloroacrylonitrile and 3-ethylacrylonitrile. Examples of an acrylate in which X is $CO_2R^8$ include methyl acrylate, ethyl acrylate, isopropyl acrylate, t-butyl acrylate, methyl methacrylate, methyl crotonate, methyl 2-chloroacrylate, methyl 3-chloroacrylate and isopropyl 3-chloroacrylate.

Examples of a nitrobenzenenitrile derivative represented by formula (3), in which X is nitrile, include 4-(2-nitrobenzene)butanonitrile, 4-(2-nitrobenzene)-2-methylbutanonitrile, 4-(2-nitrobenzene)-3-methylbutanonitrile, 4-(2-nitrobenzene)-3-ethylbutanonitrile, 4-(2-nitrobenzene)-3-chlorobutanonitrile, 4-(2-nitrobenzene)-n-heptanonitrile, 4-(2-nitro-3-isopropylbenzene)butanonitrile, 4-(2-nitro-3-butylbenzene)butanonitrile, 4-(2-nitro-4-t-butylbenzene)butanonitrile, 4-(2-nitro-5-methylbenzene)butanonitrile and 4-(2-nitro-3-methylbenzene)-2-methylbutanonitrile. In particular, 4-(2-nitrobenzene)butanonitrile is preferable because it can be converted into a 5-nitro-1-tetralone which used in a variety of applications.

Examples of a nitrobenzenecarboxylic acid represented by formula (3) where X is carboxyl, include 4-(2-nitrobenzene)butyric acid, 4-(2-nitrobenzene)-2-methylbutyric acid, 4-(2-nitrobenzene)-3-methylbutyric acid, 4-(2-nitrobenzene)-3-ethylbutyric acid, 4-(2-nitrobenzene)-3-chlorobutyric acid, 4-(2-nitro-3-isopropylbenzene)butyric acid, 4-(2-nitro-3-butylbenzene) butyric acid, 4-(2-nitro-4-t-butylbenzene)butyric acid, 4-(2-nitro-5-methylbenzene)butyric acid, 4-(2-nitro-5-methylbenzene)butyric acid and 4-(2-nitro-3-methylbenzene)-2-methylbutyric acid. In particular, 4-(2-nitrobenzene)butyric acid is preferable because it can be converted into a 5-nitro-1-tetralone which is used in a variety of applications.

Examples of a nitrobenzenecarboxylate represented by formula (3) where X is $CO_2R^8$ include methyl 4-(2-nitrobenzene)butyrate, methyl 4-(2-nitrobenzene)-2-methylbutyrate, methyl 4-(2-nitrobenzene)-3-methylbutyrate, methyl 4-(2-nitrobenzene)-3-ethylbutyrate, methyl 4-(2-nitrobenzene)-3-chlorobutyrate, methyl 4-(2-nitro-3-isopropylbenzene) butyrate, methyl 4-(2-nitro-3-butylbenzene) butyrate, methyl 4-(2-nitro-4-t-butylbenzene) butyrate, methyl 4-(2-nitro-5-methylbenzene) butyrate, methyl 4-(2-nitro-3-methylbenzene)-2-methylbutyrate, ethyl 4-(2-nitrobenzene)butyrate, ethyl 4-(2-nitrobenzene)-2-methylbutyrate, ethyl 4-(2-nitrobenzene)-3-methylbutyrate, ethyl 4-(2-nitrobenzene)-3-ethylbutyrate, ethyl 4-(2-nitrobenzene)-3-chlorobutyrate, ethyl 4-(2-nitro-3-isopropylbenzene) butyrate, ethyl 4-(2-nitro-3-butylbenzene) butyrate, ethyl 4-(2-nitro-4-t-butylbenzene) butyrate, ethyl 4-(2-nitro-5-methylbenzene) butyrate, ethyl 4-(2-nitro-3-methylbenzene)-2-methylbutyrate, cyclohexyl 4-(2-nitrobenzene)butyrate, phenyl 4-(2-nitrobenzene) butyrate and benzyl 4-(2-nitrobenzene)butyrate. In particular, methyl and ethyl 4-(2-Nitrobenzene)butyrate are preferable because they can be readily converted into a 5-nitro-1-tetralone which is used in a variety of applications.

Examples of a nitrobenzenecarboxamide represented by formula (3) where X is $CONH_2$, include 4-(2-nitrobenzene) butyramide, 4-(2-nitrobenzene)-2-methyl butyramide, 4-(2-nitrobenzene)-3-methylbutyramide, 4-(2-nitrobenzene)-3-ethyl butyramide, 4-(2-nitrobenzene)-3-chlorobutyramide, 4-(2-nitrobenzene)-heptyramide, 4-(2-nitro-3-isopropylbenzene)butyramide, 4-(2-nitro-3-butylbenzene) butyramide, 4-(2-nitro-4-t-butylbenzene)butyramide, 4-(2-nitro-5-methylbenzene)butyramide, 4-(2-nitro-5-methylbenzene)butyramide, 4-(2-nitro-3-methylbenzene)-2-methylbutyramide and 4-(2-nitro-5-methylbenzene)-valeramide. In particular, 4-(2-nitrobenzene)butyramide is preferable because it can be converted into a 5-nitro-1-tetralone, which is used in a variety of applications.

The compounds represented by formulas (1) to (3) are not limited to those described above.

A nitrobenenecarboxamide represented by formula (3) where X is $CONH_2$ can be prepared by reacting a nitrobenzenenitrile derivative represented by formula (3) where X is nitrile with water under acidic conditions. An acid used for reaction of the nitrobenzenenitrile derivative with water under acidic conditions may be any acid by which the nitrile group can be protonated; for example, sulfuric acid and sulfonic acids such as p-toluenesulfonic acid, chlorosulfonic acid, trifluoromethanesulfonic acid. Sulfuric acid is preferable because it is inexpensive and readily available. The amount of the acid used must be one or more equivalent to the nitrobenzenenitrile derivative. The reaction is initiated by contacting the nitrobenzenenitrile derivative with the acid under anhydrous conditions. A contact temperature and a contact period may vary depending on the type and the amount of the acid. For example, when using 20 equivalents of sulfuric acid, the reaction can be substantially completed by treatment at 100° C. for 4 hours. In the reaction, a solvent may be used, which must be inert during the reaction. A reaction pressure may be an ambient, increased or reduced pressure as long as a proper reaction temperature can be maintained.

Then, the mixture of the acid and the nitrobenzenenitrile derivative can be reacted with water to provide a nitrobenzenecarboxamide. The amount of water used must be one or more equivalent to the nitrobenzenenitrile derivative. A reaction temperature may vary depending on the type of the acid, but a lower temperature is generally advantageous. If the reaction is conducted at an elevated temperature, the nitrobenzenecarboxamide may be further hydrolyzed into a corresponding nitrobenzenecarboxylic acid. A reaction temperature is 50 to 200° C., preferably 50 to 150° C. A reaction period may be quite short; specifically, 5 min or less is sufficient. A longer reaction period may lead to hydrolysis to the nitrobenzenecarboxylic acid as is at a higher reaction temperature. As described above, a reaction temperature and a reaction period must be carefully chosen. Herein, water containing a basic compound may be used. Specifically, water containing a basic compound may be added, or alternatively a basic compound or water containing a basic compound may be added after adding water. By adding a basic compound, a higher reaction temperature and a longer reaction period may be employed while preventing hydrolysis into a nitrobenzenecarboxylic acid derivative.

A nitrobenzenecarboxamide may be obtained as crystals after reacting with water when it has a higher melting point or is highly crystallizable. The crystals may be washed with water for removing the acid, salts and/or the basic compound. If necessary, the crystals are purified by, for example, recrystallization. When a melting point is too low to give crystals after reaction with water, the product may be extracted, concentrated as usual, and then isolated by, for example, distillation or recrystallization. These treatments or reactions are preferably conducted in a liquid phase, and may be conducted batchwise or in a continuous system.

Alternatively, a nitrobenzenecarboxamide may be prepared by reacting a nitrobenzene carboxylic acid represented by formula (3) where X is carboxyl and/or its derivative (an ester or acid halide), with ammonia.

When directly reacting the nitrobenzenecarboxylic acid with ammonia, a compound which can act as a dehydrating agent or a condensing agent such as DCC may be used. In the reaction without a condensing agent, the system must be heated. The reaction may be conducted either in a liquid or a gaseous phase, but a liquid phase is preferable in the light of a volumetric efficiency. Although the reaction may be conducted without a solvent, ammonia liquefied in an autoclave may be used as a solvent or alternatively a solvent inert to the reaction may be added. A reaction temperature and a reaction period may vary depending on the type of a dehydrating agent or condensing agent used. A reaction pressure is preferably an ambient pressure or higher.

When reacting an ester of a nitrobenzenecarboxylic acid with ammonia, a catalyst may be added. Without a catalyst, the reaction system must be heated. The reaction may be conducted either in a liquid phase or in a gaseous phase, but a liquid phase is preferable in the light of a volmetric efficiency. Although the reaction may be conducted without a solvent, ammonia liquefied in an autoclave may be used as a solvent or alternatively a solvent inert to the reaction may be added. A reaction temperature and a reaction period may vary depending on the type of a catalyst used. A reaction pressure is preferably an ambient pressure or higher.

When reacting an acid halide of a nitrobenzenecarboxylic acid with ammonia, a catalyst may be added, a desalting agent may be added, or an excessive ammonia may be added as a desalting agent. The reaction may be conducted either in a liquid phase or in a gaseous phase, but a liquid phase is preferable in the light of a volmetric efficiency. Although the reaction may be conducted without a solvent, ammonia liquefied in an autoclave may be used as a solvent or alternatively a solvent inert to the reaction may be added. A reaction temperature and a reaction period may vary depending on the type of a catalyst or desalting agent used. A reaction pressure is preferably an ambient pressure or higher.

These reactions may be conducted batchwise or in a continuous system.

The reaction of the compounds represented by formulas (1) and (2) in the first step in the process according to the present invention is conducted in the presence of a base, preferably a strong base. Examples of such a strong base include solid bases such as NaOH, KOH, LiOH, $Na_2CO_3$, $K_2CO_3$, $CH_3ONa$, t-BuOK, NaH, $C_6H_5ONa$, $(CH_3)_4N^+OH-$, $(Bu)_4N^+OH-$, DBU and basic ion-exchange resins, particularly preferably NaOH and KOH.

Examples of a solvent capable of dissolving at least part of a base used include circular urea derivatives such as 1,3-dimethyl-2-imidazolidinone, 1,3-diethyl-2-imidazolidinone, 1,3-dipropyl-2-imidazolidinone and 1,3-dibutyl-2-imidazolidinone; amides such as formamide, N-methylformamide, N,N-dimethylformamide, N-methylacetamide, N,N-dimethylacetamide and hexamethylphosphoramide; dimethylsulfoxide; sulfolane; pyridine; morpholine; ethers such as tetrahydrofuran and 1,4-dioxane; nitrites such as acetonitrile and propionitrile; and lower alcohols such as methanol, ethanol and isopropanol. These solvents may be mixed with water or used in combination of two or more for improving a solubility of a base. When using a catalyst capable of solubilizing a base, any solvent which is inert to the reaction may be used. An example of a preferable solvent is a mixture of 1,3-dimethyl-2-imidazolidinone and water.

An example of a catalyst capable of solubilizing a base is a phase transfer catalyst. Examples of a phase transfer catalyst include cetyltrimethylammonium bromide, tetrabutylammonium chloride, tetrabutylammonium bromide and tetrabutylammonium hydroxide.

When reacting the compounds represented by formulas (1) and (2) as the starting materials in the presence of a base in the first step of the process according to the present invention, a molar ratio of the starting materials is preferably base/ortho-alkylnitrobenzene derivative/acrylonitrile derivative=0.01 to 1.0/1/0.1 to 5 for preparation of a nitrobenzenenitrile derivative represented by formula (2) where X is nitrile; and base/ortho-alkylnitrobenzene derivative/acrylate=0.01 to 1.0/1/0.1 to 10 for preparation of a nitrobenzenecarboxylate represented by formula (2) where X is $CO_2R^8$.

When reacting the compounds represented by formulas (1) and (2) as the starting materials in the presence of a base in the first step of the process according to the present invention, the amount of a solvent capable of dissolving at least part of a base is 0.1 to 20 weight parts, preferably 0.5 to 20 weight parts to one part of an ortho-alkylnitrobenzene derivative, and the amount of a catalyst capable of solubilizing a base is 0.1 to 10 mole % to the ortho-alkylnitrobenzene derivative.

When reacting the compounds represented by formulas (1) and (2) as the starting materials in the presence of a base in the first step of the process according to the present invention, a reaction temperature may vary depending on a base and a solvent used, but is preferably 150° C. or lower because the reaction must be conducted at a temperature equal to or lower than a decomposition temperature of an ortho-alkylnitrobenzene derivative. A reaction period may be generally 1 min to 6 hours.

When reacting the compounds represented by formulas (1) and (2) as the starting materials in the presence of a base in the first step of the process according to the present invention, a reaction pressure may be an ambient, increased or reduced pressure as long as the starting materials or the solvent may not be removed from the system, and may be generally an ambient pressure.

The reaction is preferably conducted in an atmosphere of an inert gas such as nitrogen or under oxygen-free conditions.

When an acrylate represented by formula (2) where X is $CO_2R^8$ is used as a starting material and a solvent is mixed with water, a reaction product contains a nitrobenzenecarboxylic acid derivative.

The reaction may be conducted batchwise or in a continuous system. The reaction may be quenched by pouring the reaction mixture into ice-water, and then the mixture is neutralized to pH 6 to 7 with an acid. After separating phases using an organic solvent, the organic solvent may be removed to provide a viscous liquid containing the desired aromatic nitro compound represented by formula (3).

Examples of an extraction solvent used include isopropyl ether, ethyl acetate, butyl acetate, carbon disulfide, carbon tetrachloride, hexane, cyclohexane, petroleum ether, toluene, xylenes, chloroform, dichloromethane, 1,2-dichloroethane, trichloroethylene, 1,2-dichlorobenzene, chlorobenzene, benzonitrile, nitromethane, nitrobenzene, anisole and diethyleneglycol dimethyl ether. Any solvent other than those described above may be used as long as it can dissolve the desired compound, can be separated from water, is stable under the phase separation process and has physical properties such as a boiling point within a preferable range.

Column chromatography or distillation at a reduced pressure of the viscous liquid thus obtained may provide a pure nitrobenzenenitrile derivative, nitrobenzenecarboxylic acid, nitrobenzenecarboxylate or nitrobenzenecarboxamide. When a mixture of a nitrobenzenecarboxylic acid and a nitrobenzenecarboxylate is obtained, each compound may be separately collected by column chromatography or distillation, or alternatively the mixture may be esterified or hydrolyzed to convert the carboxylic acid into the ester or the ester into the carboxylic acid before the collection.

These compounds may be collected and purified by recrystallization or column chromatography when they have a high melting point or are easily crystallized, or by distillation at a reduced pressure or column chromatography when they have a low melting point or are poorly crystallized and exhibit good thermal stability.

Examples of an aromatic nitro compound represented by formula (3) include 4-(2-nitrobenzene)butanonitrile, 4-(2-nitrobenzene)-2-methylbutanonitrile, 4-(2-nitrobenzene)-3-methylbutanonitrile, 4-(2-nitrobenzene)-3-ethylbutanonitrile, 4-(2-nitrobenzene)-3-chlorobutanonitrile, 4-(2-nitro-3-isopropylbenzene)butanonitrile, 4-(2-nitro-3-butylbenzene)butanonitrile, 4-(2-nitro-4-t-butylbenzene)butanonitrile, 4-(2-nitro-5-methylbenzene)butanonitrile, 4-(2-nitro-3-methylbenzene)-2-methylbutanonitrile, 4-(2-nitro-5-isopropylbenzene)butanonitrile, 4-(2-nitro-5-chlorobenzene)butanonitrile, 4-(2-nitrobenzene)butyric acid, 4-(2-nitrobenzene)-2-methylbutyric acid, 4-(2-nitrobenzene)-3-methylbutyric acid, 4-(2-nitrobenzene)-3-ethylbutyric acid, 4-(2-nitro-5-isopropylbenzene)butyric acid, 4-(2-nitro-5-chlorobenzene) butyric acid, 4-(2-nitrobenzene)-3-chlorobutyric acid, 4-(2-nitro-3-isopropylbenzene)butyric acid, 4-(2-nitro-3-butylbenzene)butyric acid, 4-(2-nitro-4-t-butylbenzene) butyric acid, 4-(2-nitro-5-methylbenzene)butyric acid, 4-(2-nitro-3-methylbenzene)-2-methylbutyric acid, methyl 4-(2-nitrobenzene)butyrate, methyl 4-(2-nitrobenzene)-2-methylbutyrate, methyl 4-(2-nitrobenzene)-3-methylbutyrate, methyl 4-(2-nitrobenzene)-3-ethylbutyrate, methyl 4-(2-nitrobenzene)-3-chlorobutyrate, methyl 4-(2-nitro-3-isopropylbenzene)butyrate, methyl 4-(2-nitro-3-butylbenzene)butyrate, methyl 4-(2-nitro-4-t-butylbenzene) butyrate, methyl 4-(2-nitro-5-methylbenzene)butyrate, methyl 4-(2-nitro-3-methylbenzene)-2-methylbutyrate, methyl 4-(2-nitro-5-isopropylbenzene)butyrate, methyl 4-(2-nitro-5-chlorobenzene)butyrate, ethyl 4-(2-nitrobenzene)butyrate, ethyl 4-(2-nitrobenzene)-2-methylbutyrate, ethyl 4-(2-nitrobenzene)-3-methylbutyrate, ethyl 4-(2-nitrobenzene)-3-ethylbutyrate, ethyl 4-(2-nitrobenzene)-3-chlorobutyrate, ethyl 4-(2-nitrobenzene) butyrate, ethyl 4-(2-nitro-3-isopropylbenzene)butyrate, ethyl 4-(2-nitro-3-butylbenzene)butyrate, ethyl 4-(2-nitro-4-t-butylbenzene)butyrate, ethyl 4-(2-nitro-5-methylbenzene) butyrate, ethyl 4-(2-nitro-3-methylbenzene)-2-methylbutyrate, ethyl 4-(2-nitro-5-isopropylbenzene) butyrate, ethyl 4-(2-nitro-5-chlorobenzene)butyrate, cyclohexyl 4-(2-nitrobenzene)butyrate, phenyl 4-(2-nitrobenzene)butyrate, benzyl 4-(2-nitrobenzene)butyrate, 4-(2-nitrobenzene)butyramide, 4-(2-nitrobenzene)-2-methylbutyramide, 4-(2-nitrobenzene)-3-methylbutyramide, 4-(2-nitrobenzene)-3-ethylbutyramide, 4-(2-nitro-5-isopropylbenzene)butyramide, 4-(2-nitro-5-chlorobenzene)butyramide, 4-(2-nitrobenzene)-3-chlorobutyramide, 4-(2-nitro-3-isopropylbenzene) butyramide, 4-(2-nitro-3-butylbenzene)butyramide, 4-(2-nitro-4-t-butylbenzene)butyramide, 4-(2-nitro-5-methylbenzene)butyramide and 4-(2-nitro-3-methylbenzene)-2-methylbutyramide. In particular, 4-(2-nitrobenzene)butanonitrile, 4-(2-nitrobenzene)butyric acid, methyl 4-(2-nitrobenzene)butyrate, ethyl 4-(2-nitrobenzene) butyrate and 4-(2-nitrobenzene)butyramide are preferable because they may be readily converted into a 5-nitro-1-tetralone which is used in a variety of applications.

There will be described the cyclization in the second step in the process according to the present invention.

The cyclization of an aromatic nitro compound represented by formula (3) into a 5-nitro-1-tetralone derivative represented by formula (4) is usually conducted using an acid catalyst. Examples of such an acid include strong acids such as sulfuric acid and polyphosphoric acid; superacids such as oleum, chlorosulfonic acid, trifluoromethanesulfonic acid and fluorosulfonic acid; and Lewis-acid-containing superacids such as fluorosulfonic acid or chlorosulfonic acid containing a small amount of, e. g., $SO_3$ or $SbF_5$. Solid superacids such as sulfated zirconia and sulfated tin oxide may be also used. The amount of the acid is one or more equivalent to the substrate represented by formula (3). The cyclization may be conducted in such an acid or in a solvent inert to the acid.

A reaction temperature is generally 20° C. to 200° C., preferably 50 to 150° C. A reaction period is generally 5 min to 15 hours, preferably 20 min to 10 hours.

A reaction pressure may be an ambient or increased pressure or, if the appropriate reaction temperature can be maintained, a reduced pressure.

The reaction may be conducted batchwise or in a continuous system.

Water is added to a reaction mixture. Phases are separated using an organic solvent. After washing the organic layer with water, the organic solvent is removed to give a crude 5-nitro-1-tetralone derivative. The acid may be recovered by distillation before adding water. The recovered acid by distillation may be reused in the cyclization. When an excessive superacid is used, the superacid is preferably removed from the reaction mixture by, for example, distillation before adding water. Since addition of water to a strong acid may be an exothermic process, water is preferably added with cooling. The acid used is diluted or decomposed with water or methanol generated together with a tetralone derivative from the cyclization (hereinafter, such a diluted or decomposed acid is referred to as a "waste acid"). For example, when using fluorosulfonic acid in the reaction, it is decomposed with water or methanol to form HF, sulfuric acid and so on. The waste acid thus generated may be used to neutralize a base used in the reaction between the compounds represented by formulas (1) and (2).

Examples of an organic solvent used herein include isopropyl ether, ethyl acetate, butyl acetate, carbon disulfide, carbon tetrachloride, hexane, cyclohexane, petroleum ether, toluene, xylenes, chloroform, dichloromethane, 1,2-dichloroethane, trichloroethylene, o-dichlorobenzene, chlorobenzene, benzonitrile, nitromethane, nitrobenzene, anisole and diethyleneglycol dimethyl ether, particularly preferably isopropyl ether, ethyl acetate and butyl acetate. Any solvent other than those described above may be used as long as it can dissolve the desired compound, can be separated from water, is stable under the phase separation process and has physical properties such as a boiling point within a preferable range.

When an aromatic nitro compound represented by formula (3) is a nitrobenzenecarboxamide, the cyclization for forming a 5-nitro-1-tetralone derivative represented by formula (4) may be conducted by contacting the material with a dehydrating agent. The dehydrating agent may be preferably acidic; for example, polyphosphoric acid and phosphorous oxides. These dehydrating agents may be used alone or in combination with the strong acid described above. A reaction temperature and a reaction period may vary depending on the types of the acid and the dehydrating agent, but it must be 200° C. or lower because an excessively elevated temperature may cause decomposition of a reaction product. A reaction pressure may be an ambient, increased or reduced pressure as long as an appropriate reaction temperature may be maintained. A reaction solvent, if used, is preferably inert in the reaction and contains a minimum amount of water. The reaction is preferably conducted in a liquid phase and may be conducted batchwise or in a continuous system.

The crude 5-nitro-1-tetralone derivative may be purified by recrystallization when it has a high melting point or is readily crystallized, or by distillation when it has a low melting point or is less crystallizable.

Examples of a 5-nitro-1-tetralone derivative represented by formula (4) include 5-nitro-1-tetralone, 5-nitro-2-methyl-1-tetralone, 5-nitro-3-methyl-1-tetralone, 5-nitro-3-ethyl-1-tetralone, 5-nitro-3-chloro-1-tetralone, 5-nitro-4-n-propyl-1-tetralone, 5-nitro-6-isopropyl-1-tetralone, 5-nitro-6-n-butyl-1-tetralone, 5-nitro-7-t-butyl-1-tetralone, 5-nitro-8-methyl-1-tetralone, 5-nitro-8-chloro-1-tetralone, 5-nitro-2,6-dimethyl-1-tetralone, 5-nitro-4,8-dimethyl-1-tetralone and 5-nitro-8-isopropyl-1-tetralone. In particular, 5-nitro-1-tetralone is preferable because it may be converted into 1,5-diaminonaphthalene.

There will be described a conversion into a 1,5-diaminonaphthalene derivative in the third step in the process according to this invention.

A 5-nitro-1-tetralone derivative represented by formula (4) may be then converted into a desired 1,5-diaminonaphthalene derivative by 1) oxime formation, conversion into a 5-nitro-1-aminonaphthalene derivative, and then reduction of the nitro groups, or 2) imine formation, aromatization and then reduction of the nitro groups.

A 5-nitro-1-tetralone derivative may be converted into an oxime by a common oxime-formation process. An oxime-forming agent may be hydroxylamine or a salt of hydroxylamine. Examples of a salt of hydroxylamine include hydroxylamine hydrochloride and hydroxylamine sulfate. Hydroxylamine may be obtained by neutralizing such a salt with a basic compound or by reacting ammonia with a peroxide such as hydrogen peroxide. Hydroxylamine may be isolated by an appropriate method such as distillation, and may be used after extraction, or directly used as it is.

A reaction solvent in the oxime formation may be any solvent which is inert in the reaction. Examples of such a solvent include alcohols and alcohols containing an acidic compound such as acetic acid.

A reaction temperature is from 20° C. to a temperature at which hydroxylamine or its salt decomposes. It is generally 20 to 150° C., preferably 50 to 120° C.

A reaction pressure may be an ambient pressure, but an increased or reduced pressure may be employed as long as an appropriate reaction temperature may be maintained.

A reaction period is 1 min or longer. A product may be isolated by an appropriate method such as distillation, recrystallization, reprecipitation and column chromatography, or some of the reaction solvent may be evaporated. Alternatively, when the reaction solvent is inert in the next step, the reaction mixture may be directly used without further concentration or isolation.

Conversion of the oxime into a 5-nitro-1-aminonaphthalene derivative may be conducted using a reagent capable of cleaving the N—O bond in the oxime group (=NOH) in a dehydration reaction. For example, the oxime may be heated in acetic acid as a solvent in the presence of hydrochloric acid to provide a desired 5-nitro-1-aminonaphthalene hydrochloride. A reaction temperature and a reaction period may vary depending on a reagent used, and may be chosen such that the N—O bond in the oxime group can be cleaved in a dehydration reaction as described above. A reaction temperature is generally 50 to 250° C., preferably 50 to 200° C. For facilitating elimination of OH, the OH in the oxime group may be converted into a functional group which may be readily eliminated, for example, into $OCOCH_3$ using acetic anhydride. A reaction pressure may be an ambient or increased pressure. When the dehydrating reagent is gaseous, it may be fed at an ambient pressure, but it is advantageously charged in a closed system at an increased pressure.

After the oxime formation, conversion into a 5-nitro-1-aminonaphthalene derivative is conducted, which may be a one-step reaction.

The nitro group may be converted into an amino group by directly using a method for converting a nitrobenzene derivative into an aniline derivative, but reduction with hydrogen using a hydrogenation catalyst is the most cost-effective process. Examples of a hydrogenation catalyst include Raney metals such as Raney Ni and Raney Co; and platinum-group catalysts such as Pd/C and Pt/alumina. The reaction may be conducted in a gaseous or liquid phase. A solvent used in a liquid phase reaction may be any inert solvent in the reaction, preferably alcohols and amides. A reaction temperature is generally an ambient temperature to 150° C., preferably 50 to 100° C. A reaction pressure may be an ambient pressure or higher, but an excessively higher hydrogen pressure may cause hydrogenation on the naphthalene ring.

All the reactions of oxime formation, conversion into an aminonaphthalene derivative and reduction of a nitro group may be conducted batchwise or in a continuous system.

Alternatively, a 5-nitro-1-tetralone derivative may be converted into a 1,5-diaminonaphthalene derivative via an imine instead of an oxime.

A 5-nitro-1-tetralone derivative may be converted into an imine by reacting the nitro compound with an excessive amount of ammonia and/or an ammonium salt. In the reaction, a dehydrating agent may be added. The reaction may be conducted at an ambient or increased pressure, but when using ammonia, the reaction is preferably conducted at an increased pressure.

Aromatization of the tetralin ring and reduction of the nitro groups after imine formation may proceed via hydrogen transfer, using a hydrogenation catalyst such as Raney metals, e. g., Raney Ni and Raney Co and platinum group catalysts, e. g., Pd/C and Pt/alumina. Hydrogenation may be conducted in the presence of hydrogen for reducing partially remaining nitro and nitroso groups. Aromatization of the tetralin ring and reduction of the nitro group may be conducted in one step. Specifically, the imine may be converted into a 1,5-diaminonaphthalene derivative using a hydrogenation catalyst in the presence of hydrogen.

Alternatively, a 5-nitro-1-tetralone derivative may be converted into a 1,5-diaminonaphthalene derivative using a hydrogenation catalyst in the presence of ammonia and/or an ammonium salt together with hydrogen.

All the reactions of imine formation, aromatization and reduction of the nitro group may be conducted in a gaseous or liquid phase, and batchwise or in a continuous system.

A product 1,5-diaminonaphthalene derivative in the present invention is a compound represented by general formula (5), where $R^1$ to $R^4$ and $R^6$ to $R^7$ are as defined in formulas (1) and (2).

Examples of a 1,5-diaminonaphthalene derivative used in the present invention include 1,5-diaminonaphthalene, 2-methyl-1,5-diaminonaphthalene, 3-methyl-1,5-diaminonaphthalene, 3-ethyl-1,5-diaminonaphthalene, 3-chloro-1,5-diaminonaphthalene, 4-n-propyl-1,5-diaminonaphthalene, 6-isopropyl-1,5-diaminonaphthalene, 6-n-butyl-1,5-diaminonaphthalene, 7-t-butyl-1,5-diaminonaphthalene, 8-methyl-1,5-diaminonaphthalene, 6-chloro-1,5-diaminonaphthalene, 2,6-dimethyl-1,5-diaminonaphthalene and 4,8-dimethyl-1,5-diaminonaphthalene.

This invention will be further described with reference to, but not limited to, Examples.

EXAMPLE 1

Preparation of a 4-(2-nitrobenzene)propane Derivative

In an ice-water bath was placed a 2 L (internal volume) four-necked flask equipped with a reflux condenser, a thermometer, a dropping funnel and a stirrer. In the flask were charged 50 g of 96% NaOH (1.2 mol) and 64 g of water, and the mixture is dissolved. To the mixture was added 1.2 L of 1,3-dimethyl-2-imidazolidinone (hereinafter, referred to as DMI), and the resulting mixture was stirred. To the mixture was added dropwise a solution of 2-nitrotoluene (164.6 g, 1.2 mol) in DMI (360 mL) from the dropping funnel over about 1 hour. Then, to the mixture was added dropwise a solution of methyl acrylate (106.5 g, 1.2 mol) in DMI (360 mL) from the dropping funnel over about 3 hours while maintaining a reaction temperature at 0 to 4° C. The reaction liquid was poured into about 5 L of ice-water. Then, sulfuric acid as a decomposition product of a superacid used in the subsequent step described in Example 2 was effectively utilized for neutralizing the base. Specifically, the mixture was neutralized to pH 5 to 7 with the residual sulfuric acid after recovering by distillation $FSO_3H$ used in cyclization of a 4-(2-nitrobenzene) propane derivative at the end of the reaction. Then, the mixture was extracted with 300 mL of ethyl acetate, the extract was dried over $Na_2SO_4$ and the residue was distilled at a reduced pressure ($4 \times 10^{-4}$ MPa) to give a viscous yellow liquid (160.6 g). Its purity as methyl 4-(2-nitrobenzene)butyrate was 99% and an yield on the basis of methyl acrylate was 60%.

Then, a 4-(2-nitrobenzene)butyric acid may be prepared by treating the above methyl ester as follows. In 200 mL of acetic acid was dissolved 55 g of methyl 4-(2-nitrobenzene) butyrate (0.247 mol). To the mixture were added 44 g of water (2.47 mol) and 5 g of 3N aqueous HCl. The mixture was heated for 5 hours under reflux for hydrolysis. After evaporating acetic acid and water from the reaction mixture, the residue was dissolved in 300 mL of ethyl acetate, and the organic layer was washed with water three times. After drying over $Na_2SO_4$, ethyl acetate was partially evaporated and the mixture was cooled to precipitate pale yellow crystals. After filtration and drying, 45 g of the product was obtained as pale yellow crystals. Its purity as 4-(2-nitrobenzene)butyric acid was 99.5%, and an yield on the basis of the ester was 87%.

EXAMPLE 2

Preparation of a 5-nitro-1-tetralone Derivative

Seventy five grams (75 g) of $FSO_3H$ was placed in 300 mL (internal volume) three-necked flask equipped with a reflux condenser, a thermometer, a dropping funnel and a magnetic stirring bar. To the stirred mixture heated in an oil bath at 100° C. was added dropwise 10.45 g of 4-(2-nitrobenzene)butyric acid from the dropping funnel over 60 min for initiating cyclization to form 5-nitro-1-tetralone.

At the end of the reaction, the flask was equipped with a short distilling column, and then 65 g of $FSO_3H$ was recovered by distillation at a reduced pressure (0.027 MPa). The recovered $FSO_3H$ did not exhibit reduced activity in the cyclization even after repeated use in the reaction. Into 500 mL of ice-water was poured a mixture containing 5-nitro-1-tetralone and sulfuric acid generated by decomposition of a part of the superacid, and the resulting mixture was extracted with butyl acetate (150 mL×2). The extract was washed with water (100 mL×3) and dried over sodium sulfate. Butyl acetate was evaporated to give brownish crystals containing 5-nitro-1-tetralone (9.0 g). A part of the crystals was taken for quantification by GC. It was thus indicated that a conversion rate of 4-(2-nitrobenzene)butyric acid was 100% and that the desired 5-nitro-1-tetralone was obtained in an yield of 68% without detecting isomers in which nitro and/or carbonyl groups were configured in a different position.

The sulfuric-acid containing solution after phase separation of the reaction mixture using butyl acetate may be effectively utilized for neutralizing the aqueous solution containing the base used in Example 1.

EXAMPLE 3

Preparation of a 1,5-diaminonaphthalene Derivative (1) Oxime Formation

In a 100 mL flask equipped with a reflux condenser were placed 2.26 g of 5-nitro-1-tetralone and 60 mL of ethanol. To the mixture was added a solution of hydroxylamine hydrochloride (1.82 g) in water (4.5 mL). The content of the flask was stirred with a stirring bar at reflux for 8 hours. After evaporating the solvent, the residue was purified by column chromatography (eluent: hexane/ethyl acetate=5/1)' to give 2.2 g of 5-nitro-1-tetralone oxime.

(2) Aminonaphthalene Formation

In a 100 mL flask equipped with a reflux condenser, an inlet tube for hydrogen chloride gas and a thermometer were placed 2.1 g of 5-nitro-1-tetralone oxime and 40 mL of acetic acid. While bubbling hydrogen chloride gas, the mixture was heated at 100° C. for 4 hours with stirring by a stirring bar. After allowing the mixture to be cooled to room temperature, a precipitated 5-nitro-1-aminonaphthalene hydrochloride was collected by filtration and rinsed with a small amount of acetic acid. After drying in vacuo, 5-nitro-1-aminonaphthalene hydrochloride (1.0 g) was obtained. No naphthalene derivatives isomerized in the amino or nitro group were detected.

(3) Reduction of a Nitro Group

To 5-nitro-1-aminonaphthalene hydrochloride were added water and ethyl acetate. To the mixture was further added a 10% aqueous sodium hydroxide until the aqueous phase became pH 8. Then, the organic phase was separated and the aqueous phase was further extracted with ethyl acetate twice. The combined organic phases were washed with an equal amount of water three times, dried over anhydrous magnesium sulfate and distilled off the solvent, to give 5-nitro-1-aminonaphthalene as a red solid.

In a 50 mL flask equipped with a gas inlet tube and a thermometer were placed 12.5 mg of 5-nitro-1-aminonaphthalene, 12 mg of 5% Pd/C (50% wet) and 5 mL of DMF. The mixture was heated to 145° C. under nitrogen stream. When the temperature reached 145° C., the gas was replaced with hydrogen gas. While bubbling hydrogen, the mixture was stirred by a stirring bar for 3 hours. After allowing the mixture to be cooled to room temperature, the catalyst was filtered off. After adding 30 mL of ethyl acetate to the filtrate, the filtrate was washed with an equal volume of water five times. The ethyl acetate solution was dried over anhydrous magnesium sulfate and distilled off the solvent. The residue was purified by preparative TLC (eluent: hexane/ethyl acetate=1/1) to 10 mg of 1,5-diaminonaphthalene as white crystals. No isomers in an amino group were detected.

EXAMPLE 4

Preparation of a 5-nitro-1-tetralone Derivative

Fifteen grams (15 g) of $FSO_3H$ was placed in 100 mL (internal volume) three-necked flask equipped with a reflux condenser, a thermometer, a dropping funnel and a magnetic stirring bar. To the stirred mixture heated in an oil bath at 100° C. was added dropwise 1.902 g of 4-(2-nitrobenzene) butanonitrile from the dropping funnel over 60 min. The reaction mixture was poured into 100 mL of ice-water, and the mixture was extracted with ethyl acetate (50 mL×2). The combined extracts were washed with water (50 mL×3), dried over sodium sulfate and distilled off the ethyl acetate to give 1.8 g of 5-nitro-1-tetralone as brownish crystals. A part of the crystals was taken for quantification by GC, indicating that a conversion rate of 4-(2-nitrobenzene)butanonitrile was 100% and that the desired 5-nitro-1-tetralone was formed in an yield of 68%. No isomers having nitro and/or carbonyl groups in different substitution positions were detected.

EXAMPLE 5

Preparation of a 5-nitro-1-tetralone Derivative

A reaction was conducted as described in Example 4, except that 2.09 g of 4-(2-nitrobenzene)butyric acid was used as a starting material. As a result, a conversion rate of 4-(2-nitrobenzene)butyric acid was 100%, the desired 5-nitro-1-tetralone was formed in an yield of 71%, and no isomers having nitro and/or carbonyl groups in different substitution positions were detected.

EXAMPLE 6

Preparation of a 5-nitro-1-tetralone Derivative

A reaction was conducted as described in Example 4, except that 2.23 g of methyl 4-(2-nitrobenzene)butyrate was used as a starting material. As a result, a conversion rate of methyl 4-(2-nitrobenzene)butyrate was 100%, the desired 5-nitro-1-tetralone was formed in an yield of 71%, and no isomers having nitro and/or carbonyl groups in different substitution positions were detected.

EXAMPLE 7

Preparation of a 5-nitro-1-tetralone Derivative

A reaction was conducted as described in Example 4, except that 2.09 g of 4-(2-nitrobenzene)butyric acid was used as a starting material and 15 g of $FSO_3H$ and 0.325 g of $SbF_5$ were used as a superacid. As a result, a conversion rate of 4-(2-nitrobenzene)butyric acid was 100%, the desired 5-nitro-1-tetralone was formed in an yield of 81%, and no isomers having nitro and/or carbonyl groups in different substitution positions were detected.

EXAMPLE 8

Preparation of a 5-nitro-1-tetralone Derivative

Fifty grams (50 g) of 95% sulfuric acid was charged in a 100 mL (internal volume) three-necked flask equipped with a reflux condenser, a thermometer, a dropping funnel and a stirrer. To the stirred mixture heated in an oil bath at 100° C. was added 2.23 g of methyl 4-(2-nitrobenzene)butyrate, and the reaction was continued for 8 hours. As a result, a conversion rate of methyl 4-(2-nitrobenzene)butyrate was 100%, the desired 5-nitro-1-tetralone was formed in an yield of 58%, and no isomers having nitro and/or carbonyl groups in different substitution positions were detected.

EXAMPLE 9

Preparation of a 5-nitro-1-tetralone Derivative

A reaction was conducted as described in Example 8, except that 50 g of polyphosphoric acid was used as an acid and the reaction time was 6 hours. As a result, a conversion rate of methyl 4-(2-nitrobenzene)butyrate was 100%, the desired 5-nitro-1-tetralone was formed in an yield of 56% and no isomers having nitro and/or carbonyl groups in different substitution positions were detected.

EXAMPLE 10

Preparation of 4-(2-nitrobenzene)butanonitrile

In an ice-water bath was placed a 2 L (internal volume) four-necked flask equipped with a reflux condenser, a thermometer, a dropping funnel and a stirrer. In the flask were charged 50 g of 96 wt % NaOH (1.2 mol) and 64 g of water, and the mixture was dissolved. To the mixture was added 1.2 L of 1,3-dimethyl-2-imidazolidinone (hereinafter, referred to as "DMI"), and the mixture was stirred. To the mixture was added dropwise a solution of ortho-nitrotoluene (164.6 g, 1.2 mol) in DMI (360 mL) from the dropping funnel over about 1 hour. To the mixture was then added dropwise a solution of acrylonitrile (31.8 g, 0.6 mol) in DMI (360 mL) from the dropping funnel over about 3 hours while maintaining a reaction temperature at 0 to 4° C. The reaction liquid was poured into about 5 L of ice-water, and the resulting mixture was neutralized with 3 N aqueous HCl to pH 5 to 6. The mixture was extracted with 300 mL of ethyl acetate, and the extract was dried over $Na_2SO_4$ and distilled at a reduced pressure ($4 \times 10^{-4}$ MPa) to give a yellow viscous liquid (63.4 g). Its purity as 4-(2-nitrobenzene)butanonitrile was 99% and an yield on the basis of acrylonitrile was 55%.

EXAMPLE 11

Preparation of Methyl 4-(2-nitrobenzene)butyrate and 4-(2-nitrobenzene)butyric Acid A reaction and work-up were conducted as described in Example 10, replacing acrylonitrile with 106.5 g of methyl acrylate (1.2 mol) to give a yellow viscous liquid (161.5 g). The viscous liquid contained a mixture of 4-(2-nitrobenzene)butyric acid and methyl 4-(2-nitrobenzene)butyrate. They might be directly separated by column chromatography or the ester alone might be collected by distillation. However, for minimizing a collection loss, the mixture was dissolved in ethyl ether, and the carboxylic acid was esterified with diazomethane into the methyl ester, which was then distilled to isolate the methyl ester with a high purity. Its purity as methyl 4-(2-nitrobenzene)butyrate was 99.5% and an yield on the basis of methyl acrylate was 60%.

The carboxylic acid may be prepared by processing the methyl ester as follows. In 200 mL of acetic acid was dissolved 55 g of methyl 4-(2-nitrobenzene)butyrate (0.247 mol). To the mixture were added 44 g of water (2.47 mol) and 5 g of 3N aqueous HCl. The mixture was heated for 5 hours under reflux for hydrolysis. After distilled off acetic acid and water from the reaction mixture, the residue was dissolved in 300 mL of ethyl acetate, and the organic layer was washed with water three times. After drying over $Na_2SO_4$, ethyl acetate was partially distilled off and the mixture was cooled to precipitate pale yellow crystals. After filtration and drying, 45 g of the product was obtained as pale yellow crystals. Its purity as 4-(2-nitrobenzene)butyric acid was 99.5%, and an yield on the basis of the ester was 87%.

EXAMPLE 12

Preparation of Methyl 4-(2-nitrobenzene)butyrate

In 1.2 L of DMI was added 31.6 g of 85 wt % powdered KOH (0.48 mol). To the stirred mixture was added dropwise 164.6 g of ortho-nitrotoluene (1.2 mol) and then 106.5 g of methyl acrylate (1.2 mol) over about 3 hours while maintaining a reaction temperature at 0 to 4° C. After work-up as described in Example 1, 115.2 g of a yellow viscous liquid was obtained. Its purity as methyl 4-(2-nitrobenzene) butyrate was 99.5%, and an yield on the basis of methyl acrylate was 43%.

EXAMPLE 13

Preparation of Methyl 4-(2-nitrobenzene)butyrate

A reaction and work-up were conducted as described in Example 12, except that the amount of 85 wt % powdered KOH was 7.9 g (0.12 mol) to give 174.1 g of a yellow viscous liquid. Its purity as methyl 4-(2-nitrobenzene) butyrate was 99.5%, and an yield on the basis of methyl acrylate was 65%.

COMPARATIVE EXAMPLE 1

Preparation of Methyl 4-(2-nitrobenzene)butyrate

A reaction and work-up were conducted as described in Example 12, except that acrylonitrile and DMI were replaced with 106.5 g of methyl acrylate (1.2 mol) and 1.2 L of DMSO, respectively. After isolation, a purity as methyl 4-(2-nitrobenzene)butyrate was 99.5%, and an yield on the basis of methyl acrylate was 3%.

EXAMPLE 14

Preparation of 4-(2-nitrobenzene)butyramide from 4-(2-nitrobenzene)butyronitrile In a 50 mL three-necked flask equipped with a reflux condenser and a thermometer were placed 0.19 g of 4-(2-nitrobenzene)butyronitrile and 1.96 of conc. sulfuric acid. With stirring using a stirring bar, the mixture was heated at 100° C. for 3 hours. At the end of heating, the hot mixture was poured into 50 mL of ice-water, and the resulting mixture was extracted with ethyl acetate (20 mL×3). The organic phase was sequentially washed with an equal volume of water, an equal volume of saturated aqueous $NaHCO_3$ solution and an equal volume of water twice. After drying over anhydrous magnesium sulfate and distilled off the extraction solvent, the residue was purified by preparative TLC (eluent: ethyl acetate) to give 0.14 g of 4-(2-nitrobenzene)butyramide.

The analysis results are as follows.

$^1$H-NMR (CDCl$_3$): 7.90 ppm (1H, d-d, J=1.1 Hz, 8.1 Hz, Ar-H), 7.53 ppm (1H, m, Ar-H), 7.37 ppm (2H, m, Ar-H), 5.40 (2H, b-s, NH$_2$), 2.94 ppm (2H, d-d, J=7.6 Hz, 10 Hz, CH$_2$), 2.33 ppm (2H, t, J=7.4 Hz, CH$_2$), 2.03 ppm (2H, m, CH$_2$);

IR (KBr): 3402, 3210, 1650, 1522, 1336 (cm$^{-1}$);

FD-MS: M/Z=209.

EXAMPLE 15

Preparation of a 5-nitro-1-tetralone Derivative

In a 10 mL flask equipped with a reflux condenser were charged 0.11 g of 4-(2-nitrobenzene)butyramide and 1.5 g of fluorosulfonic acid. With stirring using a stirring bar, the mixture was heated at 100° C. for 1 hour. The reaction mixture was poured into 20 mL of ice-water, solid $NaHCO_3$ was added to the mixture until pH=8, and the mixture was extracted with ethyl acetate (10 mL×3). After washing with water (30 mL×2), the organic layer was dried over anhydrous magnesium sulfate and distilled off the solvent. The residue was purified by preparative TLC (eluent: hexane/ethyl acetate=2/1) to give 0.02 g of 5-nitro-1-tetralone. No isomers having a nitro group at a different substitution position were formed.

(Effect of the Invention)

In a process where an ortho-alkylnitrobenzene derivative and a vinyl compound as starting materials are used to prepare a corresponding 1,5-diaminonaphthalene derivative via a 5-nitro-1-tetralone derivative, the ortho-alkylnitrobenzene derivative and a vinyl compound having an electron withdrawing group such as an acrylonitrile derivative and an acrylate may be reacted in the presence of a strong base to safely and cost-effectively provide an aromatic nitro compound such as a nitrobenzenenitrile derivative, a nitrobenzenecarboxylate, a nitrobenzenecarboxylic acid and a nitrobenzenecarboxamide. Furthermore, a 4-(2-nitrobenzene)butanonitrile derivative, a 4-(2-nitrobenzene)butyric acid derivative, a 4-(2-nitrobenzene)butyrate or a 4-(2-nitrobenzene)butyramide derivative as a starting material may be cyclized to provide a 5-nitro-1-tetralone derivative in a high yield. Furthermore, a 5-nitro-1-tetralone derivative may be used as a starting material to provide a corresponding 1,5-diaminonaphthalene derivative without forming any isomer.

What is claimed is:

1. A process for preparing a 1,5-diaminonaphthalene derivative comprising:

(i) the first step comprising reacting an ortho-alkylnitrobenzene represented by formula (1):

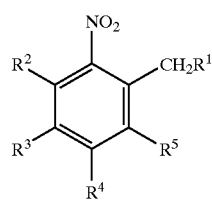

(1)

wherein $R^1$ to $R^4$, which may be the same or different, represent hydrogen, alkyl having 1 to 4 carbon atoms, aromatic hydrocarbon having 6 to 12 carbon atoms, or halogen; and $R^5$ represents hydrogen, with a vinyl compound represented by formula (2):

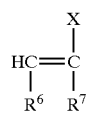

(2)

wherein $R^6$ and $R^7$, which may be the same or different, represent hydrogen, alkyl having 1 to 4 carbon atoms, or halogen; and X represents an electron withdrawing group, provided that $R^6$ and $R^7$ are mutually cis- or trans-configured, in the presence of a base, to produce an aromatic nitro compound represented by formula (3):

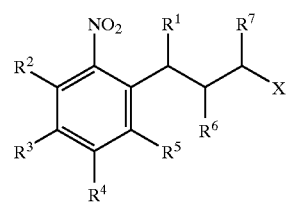

(3)

wherein $R^1$ to $R^7$ are as defined in formulas (1) and (2); and X represents an electron withdrawing group, which may be the same as or different from X as defined in formula (2);

(ii) the second step of cyclizing the aromatic nitro compound represented by formula (3) to produce a 5-nitro-1-tetralone derivative represented by formula (4):

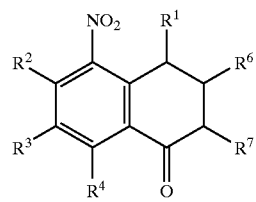

(4)

wherein $R^1$ to $R^4$ and $R^6$ to $R^7$ are as defined in formulas (1) and (2); and (iii) the third step comprising reacting the 5-nitro-1-tetralone derivative represented by formula (4) with an amine to provide an intermediate, which is then reduced and aromatized to produce the 1,5-diaminonaphthalene derivative represented by formula (5):

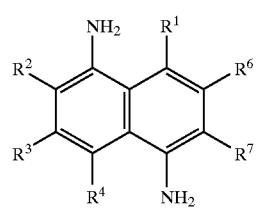

(5)

wherein $R^1$ to $R^4$ and $R^6$ to $R^7$ are as defined in formulas (1) and (2).

2. The process as claimed in claim 1, wherein X in formula (2) is one selected from the group consisting of CN and $CO_2R^8$ where $R^8$ represents alkyl having 1 to 7 carbon atoms, cycloalkyl, aromatic hydrocarbon having 6 to 12 carbon atoms or aralkyl.

3. The process as claimed in claim 1, wherein X in formula (3) is one selected from the group consisting of $CONH_2$, CN, $CO_2H$ and $CO_2R^8$ where $R^8$ represents alkyl having 1 to 7 carbon atoms, cycloalkyl, aromatic hydrocarbon having 6 to 12 carbon atoms or aralkyl.

4. The process is claimed in claim 2, wherein the reaction of the ortho-alkylnitrobenzene represented by formula (1) with the vinyl compound represented by formula (2) in the first step is conducted in the presence of at least one selected from the group consisting of a solvent capable of dissolving at least part of the base and a catalyst capable of solubilizing the base.

5. The process as claimed in claim 4, wherein the solvent capable of dissolving at least part of the base is a cyclic urea derivative.

6. The process as claimed in claim 5, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

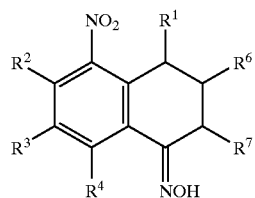

wherein R¹ to R⁴ and R⁶ to R⁷ are as defined in formulas (1) and (2), which is then converted by aromatization into a 5-nitro-1-aminonaphthalene derivative represented by formula (7):

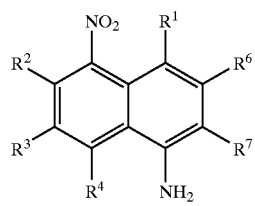

wherein R¹ to R⁴ and R⁶ to R⁷ are as defined in formulas (1) and (2), which is then reduced into the 1,5-diaminonaphthalene derivative represented by formula (5).

7. The process as claimed in claim 5, wherein in the third step, an ammonia derivative as the amine is reacted with the 5-nitro-1-tetralone derivative represented by formula (4) to provide an imine represented by formula (8):

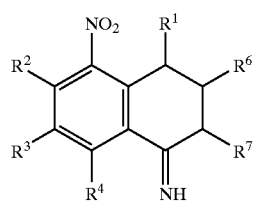

wherein R¹ to R⁴ and R⁶ to R⁷ are as defined in formulas (1) and (2), which is then reduced and aromatized to provide the 1,5-diaminonaphthalene derivative represented by formula (5).

8. The process as claimed in claim 1, wherein the reaction of the ortho-alkylnitrobenzene represented by formula (1) with the vinyl compound represented by formula (2) in the first step is conducted in the presence of at least one selected from the group consisting of a solvent capable of dissolving at least part of the base and a catalyst capable of solubilizing the base.

9. The process as claimed in claim 8, wherein the solvent capable of dissolving at least part of the base is a cyclic urea derivative.

10. The process as claimed in claim 4, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

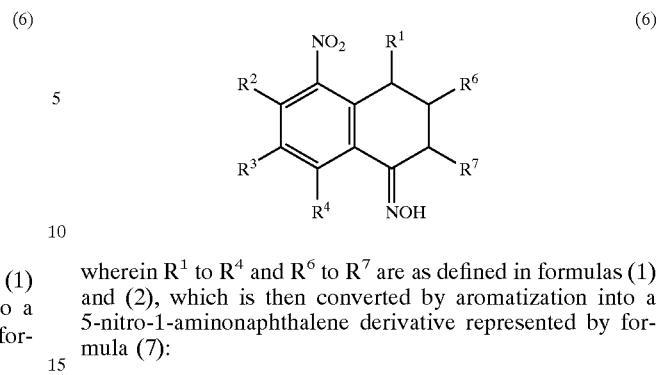

wherein R¹ to R⁴ and R⁶ to R⁷ are as defined in formulas (1) and (2), which is then converted by aromatization into a 5-nitro-1-aminonaphthalene derivative represented by formula (7):

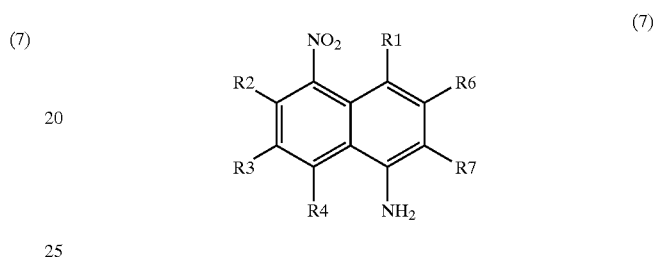

wherein R¹ to R⁴ and R⁶ to R⁷ are as defined in formulas (1) and (2), which is then reduced into the 1,5-diaminonaphthalene derivative represented by formula (5).

11. The process as claimed in claim 3, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

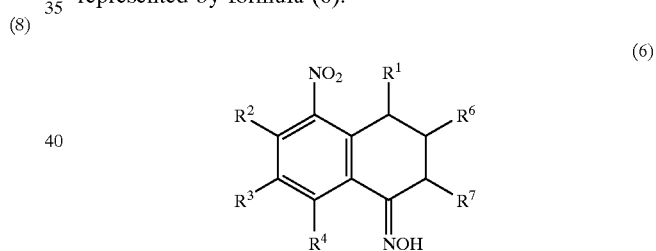

wherein R¹ to R⁴ and R⁶ to R⁷ are as defined in formulas (1) and (2), which is then converted by aromatization into a 5-nitro-1-aminonaphthalene derivative represented by formula (7):

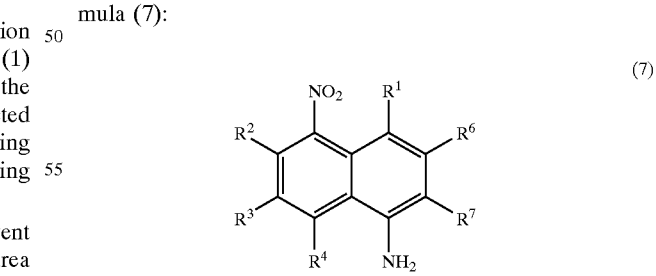

wherein R¹ to R⁴ and R⁶ to R⁷ are as defined in formulas (1) and (2), which is then reduced into the 1,5-diaminonaphthalene derivative represented by formula (5).

12. The process as claimed in claim 2, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

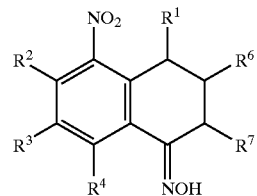

(6)

wherein $R^1$ to $R^4$ and $R^6$ to $R^7$ are as defined in formulas (1) and (2), which is then converted by aromatization into a 5-nitro-1-aminonaphthalene derivative represented by formula (7):

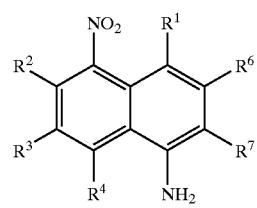

(7)

wherein $R^1$ to $R^4$ and $R^6$ to $R^7$ are as defined in formulas (1) and (2), which is then reduced into the 1,5-diaminonaphthalene derivative represented by formula (5).

13. The process as claimed in claim 1, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

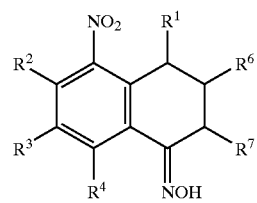

(6)

wherein $R^1$ to $R^4$ and $R^6$ to are as defined in formulas (1) and (2), which is then converted by aromatization into a 5-nitro-1-aminonaphthalene derivative represented by formula (7):

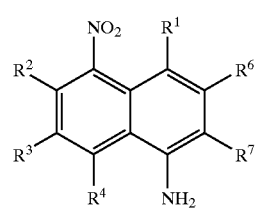

(7)

wherein $R^1$ to $R^4$ and $R^6$ to $R^7$ are as defined in formulas (1) and (2), which is then reduced into the 1,5-diaminonaphthalene derivative represented by formula (5).

14. The process as claimed in claim 9, wherein in the third step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

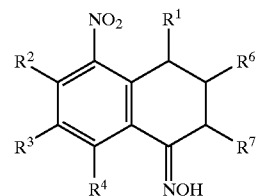

(6)

wherein $R^1$ to $R^4$ and $R^6$ to $R^7$ are as defined in formulas (1) and (2), which is then converted by aromatization into a 5-nitro-1-aminonaphthalene derivative represented by formula (7):

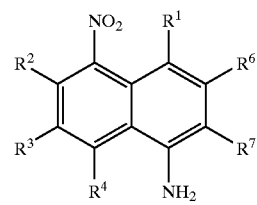

(7)

wherein $R^1$ to $R^4$ and $R^6$ to $R^7$ are as defined in formulas (1) and (2), which is then reduced into the 1,5-diaminonaphthalene derivative represented by formula (5).

15. The process as claimed in claim 8, wherein in the step, a hydroxylamine derivative as the amine is reacted with the 5-nitro-1-tetralone derivative represented by formula (4) or an ammonia derivative as the amine is reacted with the 5-nitro-1-tetralone derivative represented by formula (4) in the presence of hydrogen peroxide, to provide an oxime represented by formula (6):

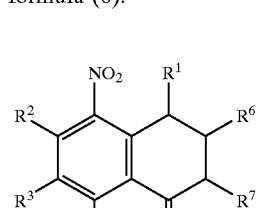

(6)

wherein $R^1$ to $R^4$ and $R^6$ to are as defined in formulas (1) and (2), which is then converted by aromatization into a 5-nitro-1-aminonaphthalene derivative represented by formula (7):

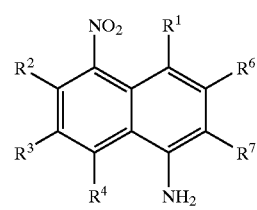

(7)

wherein $R^1$ to $R^4$ and $R^6$ to $R^7$ are as defined in formulas (1) and (2), which is then reduced into the 1,5-diaminonaphthalene derivative represented by formula (5).

16. The process as claimed in claim 4, wherein in the third step, an ammonia derivative as the amine is reacted with the 5-nitro-1-tetralone derivative represented by formula (4) to provide an imine represented by formula (8):

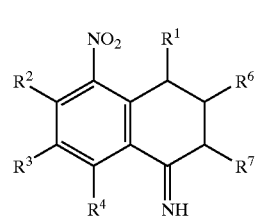

(8)

wherein $R^1$ to $R^4$ and $R^6$ to $R^7$ are as defined in formulas (1) and (2), which is then reduced and aromatized to provide the 1,5-diaminonaphthalene derivative represented by formula (5).

17. (Previously added) The process as claimed in claim 3, wherein in the third step, an ammonia derivative as the amine is reacted with the 5-nitro-1-tetralone derivative represented by formula (4) to provide an imine represented by formula (8):

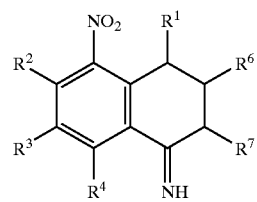

(8)

wherein $R^1$ to $R^4$ and $R^6$ to $R^7$ are as defined in formulas (1) and (2), which is then reduced and aromatized to provide the 1,5-diaminonaphthalene derivative represented by formula (5).

18. The process as claimed in claim 2, wherein in the third step, an ammonia derivative as the amine is reacted with the 5-nitro-1-tetralone derivative represented by formula (4) to provide an imine represented by formula (8):

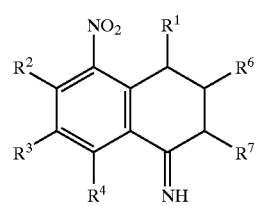

(8)

wherein $R^1$ to $R^4$ and $R^6$ to $R^7$ are as defined in formulas (1) and (2), which is then reduced and aromatized to provide the 1,5-diaminonaphthalene derivative represented by formula (5).

19. The process as claimed in claim 1, wherein in the third step, an ammonia derivative as the amine is reacted with the 5-nitro-1-tetralone derivative represented by formula (4) to provide an imine represented by formula (8):

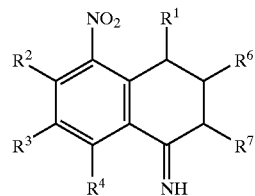

(8)

wherein $R^1$ to $R^4$ and $R^6$ to $R^7$ are as defined in formulas (1) and (2), which is then reduced and aromatized to provide the 1,5-diaminonaphthalene derivative represented by formula (5).

20. The process as claimed in claim 9, wherein in the third step, an ammonia derivative as the amine is reacted with the 5-nitro-1-tetralone derivative represented by formula (4) to provide an imine represented by formula (8):

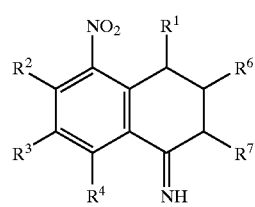

(8)

wherein $R^1$ to $R^4$ and $R^6$ to $R^7$ are as defined in formulas (1) and (2), which is then reduced and aromatized to provide the 1,5-diamninonaphthalene derivative represented by formula (5).

21. The process as claimed in claim 8, wherein in the third step, an ammonia derivative as the amine is reacted with the 5-nitro-1-tetralone derivative represented by formula (4) to provide an imine represented by formula (8):

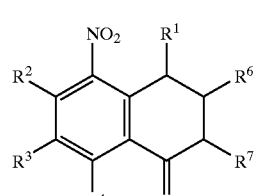

(8)

wherein $R^1$ to $R^4$ and $R^6$ to $R^7$ are as defined in formulas (1) and (2), which is then reduced and aromatized to provide the 1,5-diaminonaphthalene derivative represented by formula (5).

* * * * *